United States Patent
Dolan et al.

(10) Patent No.: US 6,629,928 B1
(45) Date of Patent: Oct. 7, 2003

(54) MODULAR TRANSDUCER CONNECTION SYSTEM

(75) Inventors: David P. Dolan, Londonderry, NH (US); Richard H. Jundanian, Methuen, MA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 10/291,059

(22) Filed: Nov. 8, 2002

(51) Int. Cl.[7] .................................................. A61B 8/00
(52) U.S. Cl. ........................................ 600/437; 600/459
(58) Field of Search ................................ 600/437–472; 73/607–623

(56) References Cited

U.S. PATENT DOCUMENTS

| | | | | |
|---|---|---|---|---|
| 4,811,740 A | * | 3/1989 | Ikeda et al. ................. | 600/437 |
| 5,205,175 A | * | 4/1993 | Garza et al. ................. | 73/628 |
| 5,209,235 A | * | 5/1993 | Brisken et al. .............. | 600/466 |
| 5,318,027 A | * | 6/1994 | Fukui ........................ | 600/437 |
| 5,505,203 A | * | 4/1996 | Deitrich et al. ............. | 600/437 |
| 5,544,660 A | * | 8/1996 | Crowley ..................... | 600/466 |
| 5,615,678 A | * | 4/1997 | Kirkham et al. ............. | 600/459 |
| 5,617,866 A | * | 4/1997 | Marian, Jr. ................. | 600/459 |
| 5,882,310 A | * | 3/1999 | Marian, Jr. ................. | 600/459 |
| 6,364,839 B1 | * | 4/2002 | Little et al. ................. | 600/459 |

* cited by examiner

Primary Examiner—Francis J. Jaworski
Assistant Examiner—William C Jung
(74) Attorney, Agent, or Firm—John Vodopia

(57) ABSTRACT

An ultrasound system, comprising: a plurality of interchangeable transducer connector modules (TCMs), wherein each TCM includes an ultrasound connector, a switching circuit, and a pluggable interface; and an ultrasound control unit, wherein the ultrasound control unit includes: a plurality of bays, each for receiving and pluggably coupling one of the TCMs into a distribution bus of the ultrasound control unit, and a system controller for selecting one of the plurality of TCMs and for activating the switching circuit of the selected TCM.

20 Claims, 5 Drawing Sheets

MODULAR TRANSDUCER CONNECTION SYSTEM

BACKGROUND OF THE INVENTION

1. Technical Field

The present invention relates generally to ultrasound systems, and more particularly relates to a modular transducer connection system that allows different types of ultrasound connectors to be readily interchanged within an ultrasound control unit.

2. Related Art

Ultrasound systems are widely used in medical offices to provide various testing functions. Accordingly, today's ultrasound systems are required to provide a great deal of flexibility, i.e., be able perform different operations throughout a medical facility. To achieve this, systems are typically configured as compact, self-contained console units that are mounted on wheels to provide mobility. Systems also include various functional features, such as on-board computers, monitors, and various input/output devices for receiving and reporting data.

Ultrasound data is obtained with an ultrasound transducer that is coupled to an ultrasound unit ("unit") via a cable thus allowing a technician to easily manipulate the location of the transducer. The transducer's cable is attachable to a connector on the unit, and can be connected and unconnected as needed. Because there are numerous uses for ultrasound, an ultrasound unit will typically include different types of transducers to perform different functions. Because each transducer comprises its own unique specifications, the connector for each transducer is often unique to the transducer type. For example, a first transducer may require 200 data lines, while another may only require 110 data lines.

Unfortunately, due to size and cost limitations, a typical ultrasound system can only be manufactured with a limited number of connector types, e.g., two or three. This limitation has several drawbacks. First, the types of testing that can be performed by the unit are limited to the types of transducers that fit the provided connectors. Secondly, newer generation units may not be able accept older legacy transducer designs without a costly modification to the unit. Such modifications may for instance require adapters to be designed, etc. Thus, today's ultrasound systems cannot effectively keep pace with technological advances. Accordingly, a system is required that will provide more flexibility for connectors in a ultrasound system.

SUMMARY OF THE INVENTION

The present invention addresses the above-mentioned problems, as well as others, by providing a modular transducer connection system that allows connector modules to be easily interchanged in an ultrasound system. In a first aspect, the present invention provides an ultrasound system, comprising: a plurality of bays, each capable of receiving different types of interchangeable transducer connector modules (TCMs), wherein each TCM includes a connector, a plurality of data lines, and a switching circuit for controlling the data lines; a distribution bus interface in each bay for electrically coupling the plurality of data lines of an inserted TCM to a distribution bus; and a system controller coupled to the distribution bus for controlling the operation of a selected TCM and for activating the switching circuit of the selected TCM.

In a second aspect, the invention provides an interchangeable ultrasound transducer connector module (TCM) that can be pluggably coupled into an ultrasound control unit, comprising: an ultrasound connector mounted on an external surface of an assembly, wherein the assembly has a predetermined configuration to mechanically mate with an opening in the ultrasound control unit; and a switching circuit mounted on an internal surface of the assembly, wherein the switching circuit electrically couples data lines in the ultrasound connector to a printed circuit board connector that can be plugged into a distribution bus within the ultrasound control unit, and wherein the switching circuit comprises a plurality of switches that can be activated and deactivated by the ultrasound control unit.

In a third aspect, the invention provides an ultrasound system, comprising: a plurality of interchangeable transducer connector modules (TCMs), wherein each TCM includes an ultrasound connector, a switching circuit, and a pluggable interface; and an ultrasound control unit, wherein the ultrasound control unit includes: a plurality of bays, each for receiving and pluggably coupling one of the TCMs into a distribution bus of the ultrasound control unit, and a system controller for selecting one of the plurality of TCMs and for activating the switching circuit of the selected TCM.

BRIEF DESCRIPTION OF THE DRAWINGS

These and other features of this invention will be more readily understood from the following detailed description of the various aspects of the invention taken in conjunction with the accompanying drawings in which.

DETAILED DESCRIPTION OF THE INVENTION

Figure 1:
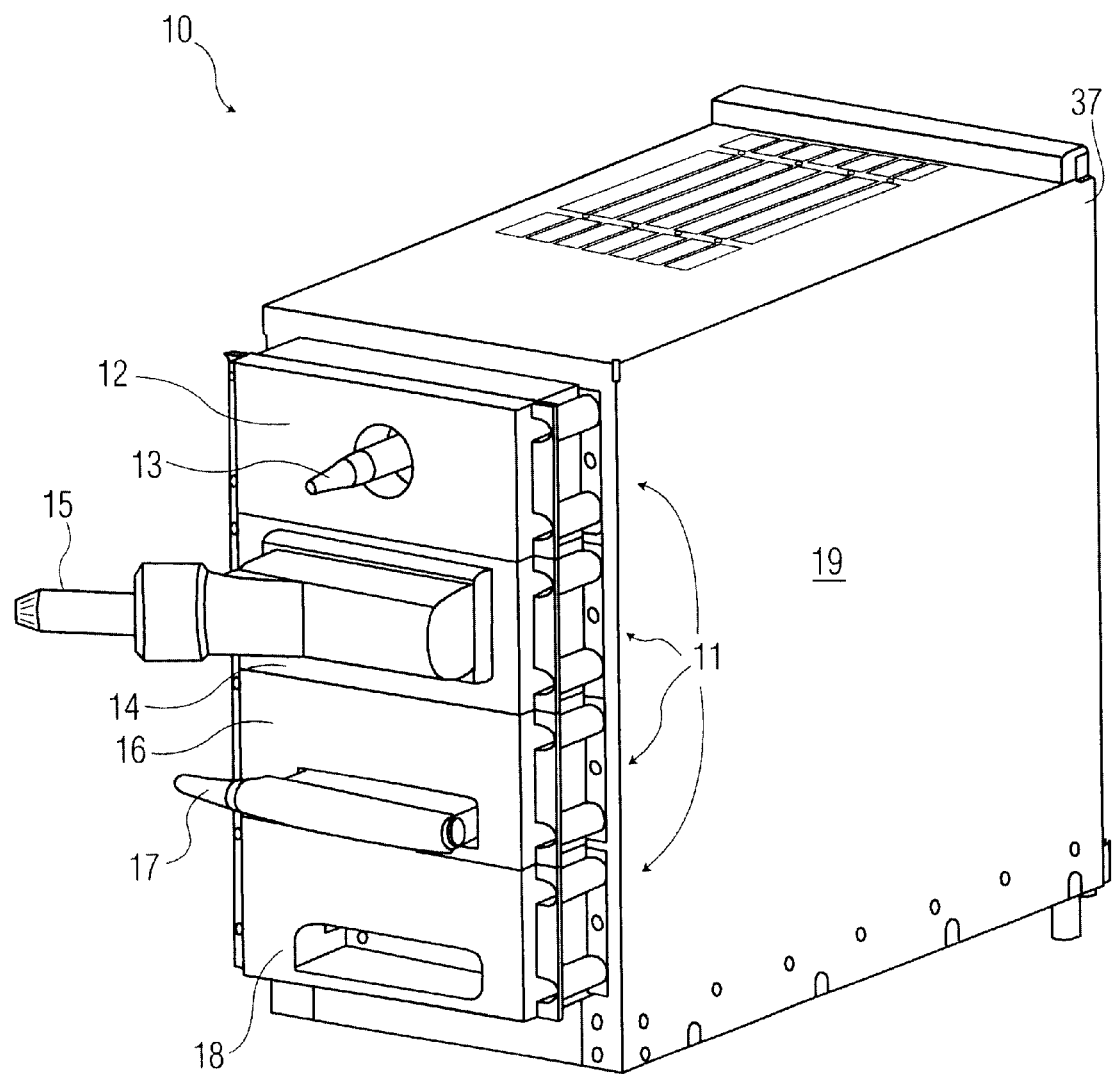
FIG. 1 depicts an enclosed ultrasound system in accordance with the present invention.

Referring now to the drawings, FIG. 1 depicts an ultrasound system 10 that includes an ultrasound control unit 19 ("unit 19") having four bays 11. System 10 further includes a plurality of interchangeable transducer connector modules (TCMs) 12, 14, 16 pluggably inserted into respective bays of unit 19. As can be seen, each TCM includes a different type of connector 13, 15, 17, to which a transducer could be attached. Also shown is a cover 18 that simply caps off an unused bay. Unit 19 is encased in an enclosure 37 to provide electromagnetic interference (EMI) shielding and mechanical support, while allowing external access to the plurality of bays. Typically, ultrasound system 10 would include other components (not shown) that are well known in the art, e.g., a wheeled console, a monitor, cables, transducers, etc. As is described in further detail below, the present invention provides a modular design that allows different TCMs to be easily inserted and/or removed from the bays 11 of unit 19.

Figure 2:
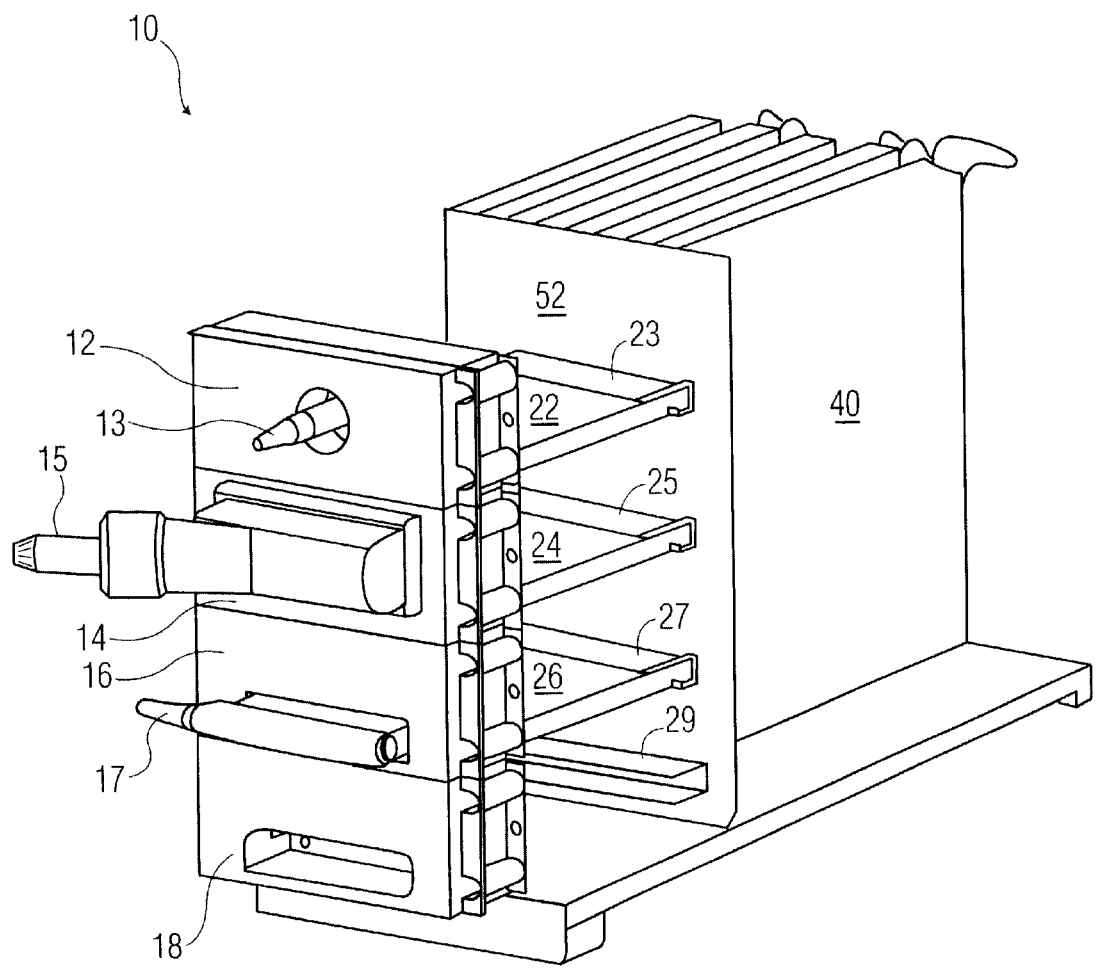
FIG. 2 depicts the ultrasound system of FIG. 1 with the enclosure removed in accordance with the present invention.

FIG. 2 depicts the ultrasound system 10 of FIG. 1, with the enclosure 17 removed. In addition to a connector 13, 15, 17, each TCM 12, 14, 16 includes a switching circuit 22, 24, 26. Switching circuits 22, 24, 26 each includes a TCM interface (described below) that can be plugged into respective distribution bus interfaces 23, 25, 27 on distribution board 52. Distribution bus interfaces 23, 25, 27, 29 may provide both mechanical and electrical coupling, thereby allowing TCMs 12, 14, 16 to be readily interchangeable. For instance, a TCM interface may comprise a male printed circuit board (pcb) connection to mate with distribution bus interfaces 23, 25, 27, which may comprise a female pcb connection. In an exemplary embodiment, distribution bus interfaces 23, 25, 27, 29 may comprise a universal configuration that could receive different configurations of TCM interfaces (e.g., 110 pin versus 200 pin). As can be seen, distribution bus interface 29 is unused since the bottom bay does not contain a TCM.

Each switching circuit 22, 24, 26 electrically couples data lines from the associated connector to the associated distribution bus interface. The number of data lines will be dependent on the type of connector. Each switching circuit also includes a set of switches that allows the data lines to be activated or deactivated, thereby enabling or disabling each TCM. The switches may be implemented in any known manner, e.g., diode switches or relays. A system controller, which includes a backplane (referred to herein as a "motherboard") and a plurality of control boards 40, can be utilized to select one of the TCMs and control its operation. Thus, when a TCM is selected, its switches are activated, and the switches in the unselected TCMs are deactivated.

Figure 3:
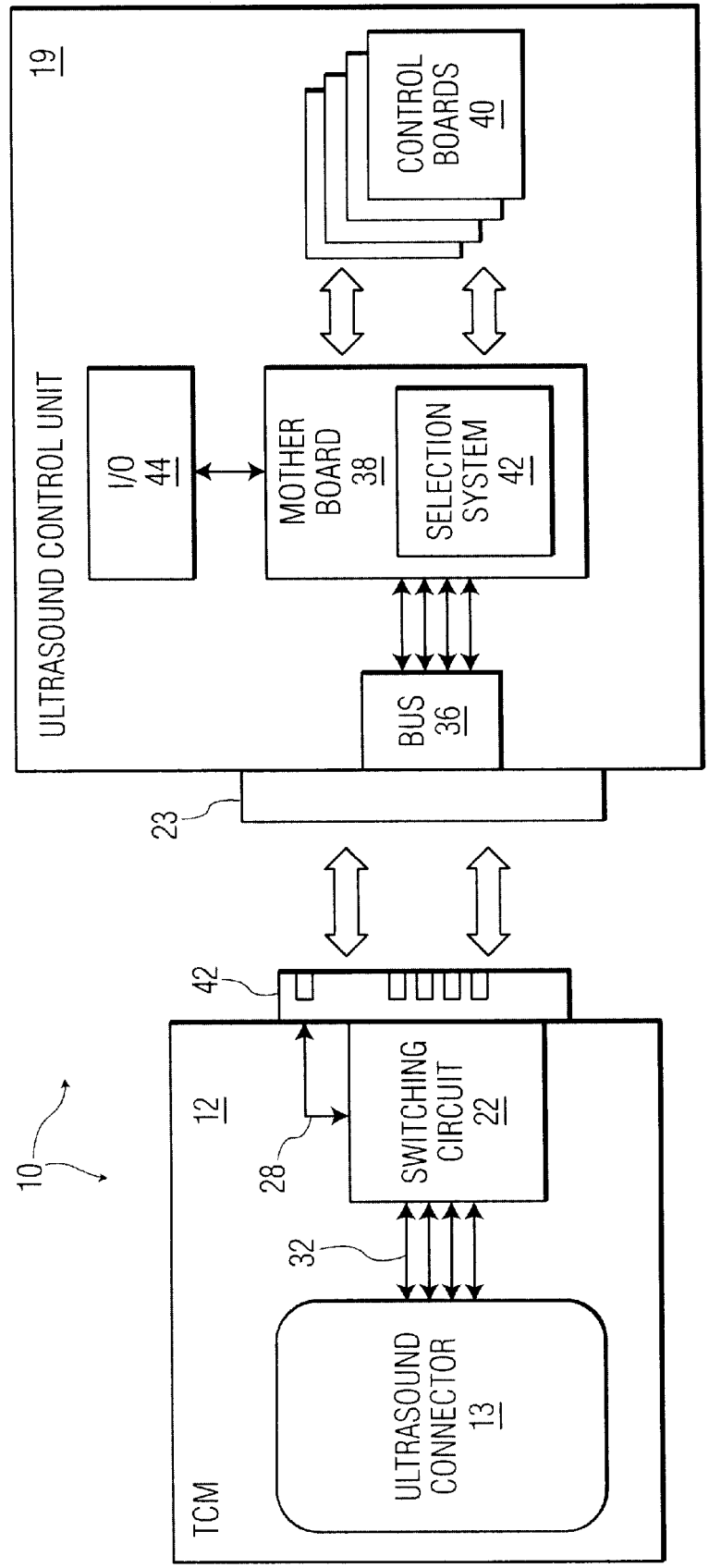
FIG. 3 depicts a system overview of an ultrasound system in accordance with the present invention.

FIG. 3 depicts an operational overview of ultrasound system 10, which includes ultrasound control unit 19 and TCM 12. It should be understood that while only a single TCM is shown in FIG. 3, the ultrasound control unit 19 would normally be configured to receive more than one TCM (as shown in FIGS. 1 and 2). Accordingly, TCM 12 was selected and is being shown for exemplary purposes only, as all TCMs share the features described herein. TCM 12 includes an ultrasound connector 13, a plurality of data lines 32, a switching circuit 22, and a TCM interface 42. One or more control lines 28 are also provided to control, i.e., activate/deactivate TCM 12. As noted above, TCM interface 42 may comprise a male pcb connector that electrically and mechanically mates with distribution bus interface 23, i.e., a female pcb connector. Thus, TCM 12 can be pluggably coupled and/or uncoupled into ultrasound control unit 19.

Within ultrasound control unit 19, distribution bus interface 23 is coupled to a distribution bus 36 that services all of the TCM interfaces 23, 25, 27, 29 (FIG. 2). The distribution bus 36 is coupled to a system controller comprised of a motherboard 38 and various modular control boards 40. Motherboard 38 includes a selection system 42 for selecting one of the plurality of available TCMs via control lines 28. An input/output (I/O) 44 is provided for receiving data from, and outputting data to, e.g., a keyboard and monitor. Motherboard 38 and control boards 40 may further comprise any computational components required to operate ultrasound system 10, e.g., a central processing unit, memory, system software, a graphics controller, signal processing systems, etc.

Figure 4:
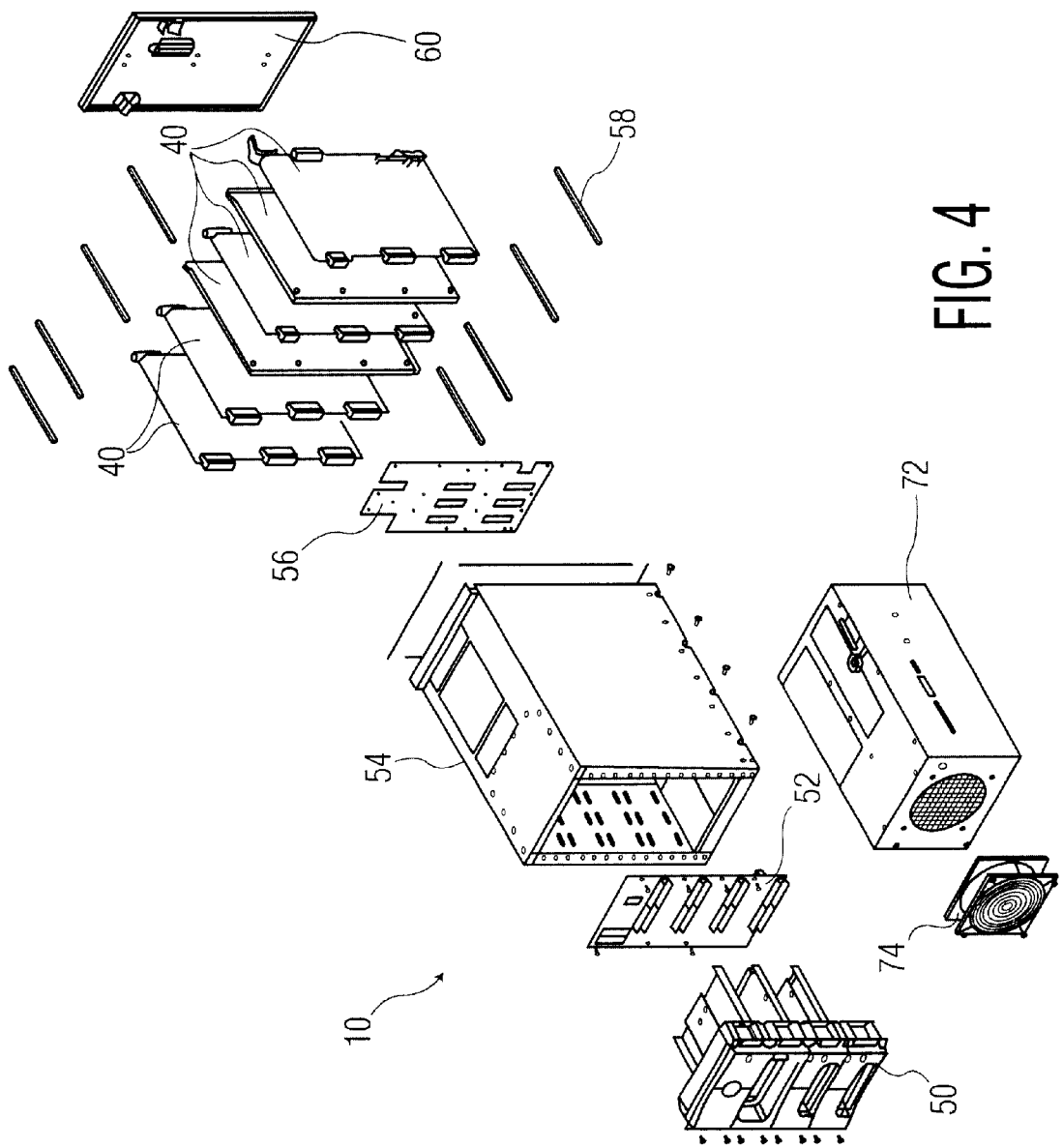
FIG. 4 depicts an exploded view of an ultrasound system in accordance with the present invention.

Referring now to FIG. 4, an exploded view of an ultrasound system 10 is shown. Specifically, a plurality of TCMs 50 are shown, which pluggably interface with distribution board 52. Distribution board 52 couples to motherboard 56, which includes card guides 58 for receiving control boards 40. An enclosure comprised of a cover 54 and rear door assembly 60 covers the electronic components and provides mechanical support as well as EMI shielding. A power supply 72 and fan 74 reside below the enclosure. It should be understood that this configuration is shown for exemplary purposes only, and that modifications to the configuration can be made without departing from the scope of the invention. For example, system 10 could include more or less than four receiving bays.

Figure 5:
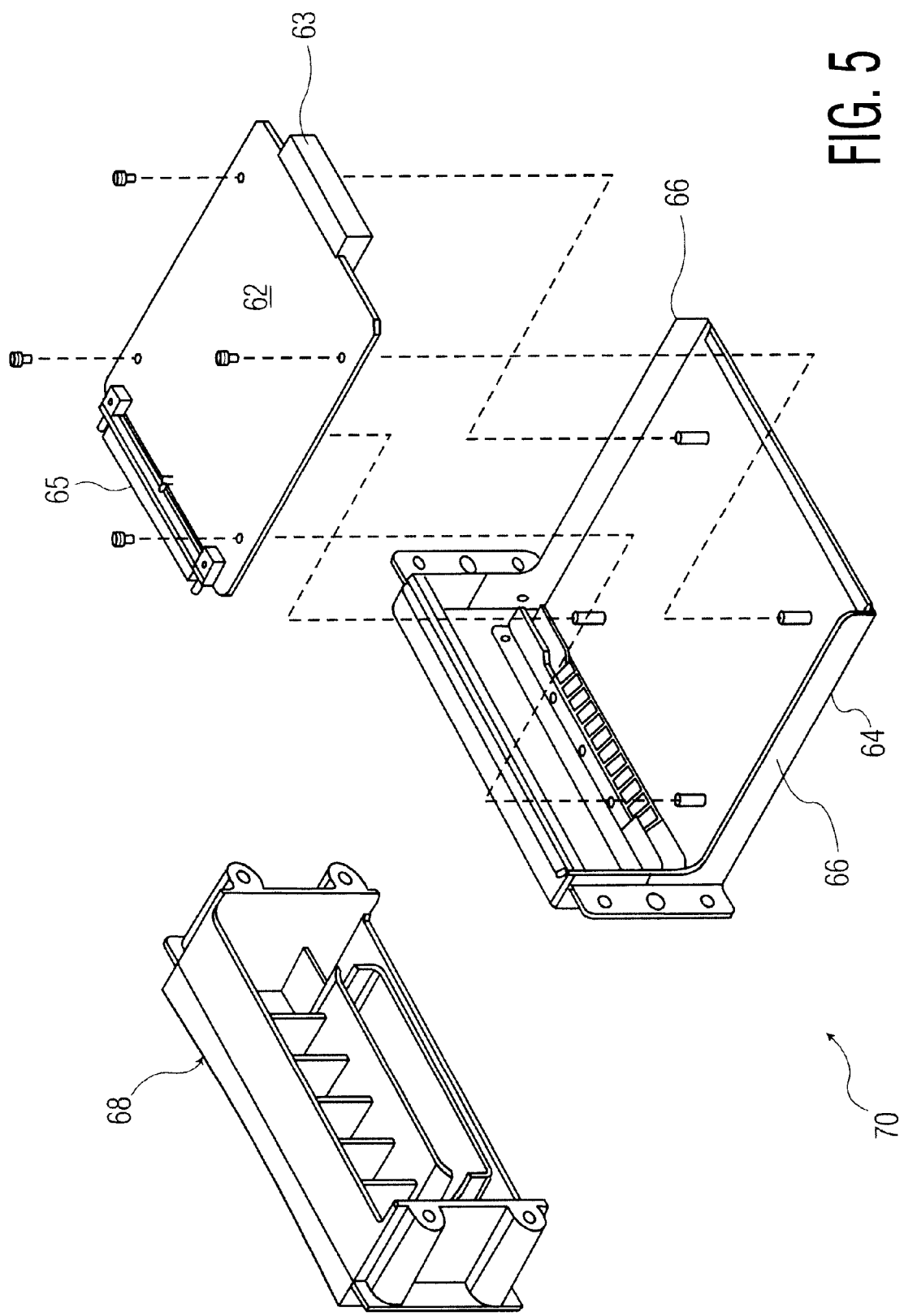
FIG. 5 depicts an exploded rear view of a transducer connector module in accordance with the present invention.

Referring now to FIG. 5, an exploded rear view of a TCM assembly 70 is shown (without a connector). TCM assembly 70 includes a tray 64 for mounting switching circuit 62. Switching circuit 62, which includes a TCM interface 63 (described above) and a connector interface 65, may be mounted to tray 64 with, e.g., a plurality of screws. Tray 64, which may typically be made from plastic or sheet metal, includes rails 66 for slideably supporting the assembly 70 in the ultrasound control unit. A front bezel 68 is provided for mounting the assembly to the opening in the ultrasound control unit. The connector (not shown) would be fastened to the front of bezel 68 and be coupled to connector interface 65.

In one embodiment, the TCM assembly 70 is configured to fit into a standard 5¼" drive bay opening found on most personal computers (PCs). However, it should be understood that no limitations exist with regard to the dimensions and configuration of the TCM assembly 70. The only requirement is that each TCM assembly within a system should share common dimensions to fit into any one of a plurality of receiving bays of a control unit.

The foregoing description of the preferred embodiments of the invention has been presented for purposes of illustration and description. They are not intended to be exhaustive or to limit the invention to the precise form disclosed, and obviously many modifications and variations are possible in light of the above teachings. Such modifications and variations that are apparent to a person skilled in the art are intended to be included within the scope of this invention as defined by the accompanying claims.

What is claimed is:

1. An ultrasound system comprising:
   a plurality of bays, each capable of receiving different types of interchangeable transducer connector modules (TCMs), wherein each TCM includes a connector, a plurality of data lines, and a switching circuit for controlling the data lines;
   a distribution bus interface in each bay for electrically coupling the plurality of data lines of an inserted TCM to a distribution bus; and
   a system controller coupled to the distribution bus for controlling the operation of a system-selected TCM and for activating the switching circuit of the system-selected TCM, wherein the system-selected TCM is selected by the system controller without the system receiving a user initiated TCM selection signal.

2. The ultrasound system of claim 1, wherein each of the plurality of bays includes a uniform opening.

3. The ultrasound system of claim 2, wherein the uniform opening comprises a personal computer standard 5¼ inch drive bay opening.

4. The ultrasound system of claim 2, wherein each different type of TCM is mounted on an assembly that mechanically mates with the uniform opening.

5. The ultrasound system of claim 1, wherein the distribution bus interface comprises a plurality of universal printed circuit board connectors that allows each different type of TCM to be plugged and unplugged from any one of the plurality of bays.

6. The ultrasound system of claim 1, wherein each of the different types of TCMs utilizes a different number of data pins.

7. The ultrasound system of claim 1, further comprising an enclosure to provide EMI shielding and mechanical support, wherein the enclosure allows external access to the plurality of bays.

8. The ultrasound system of claim 1, wherein the system controller comprises a backplane having an interface for receiving a plurality of control boards.

9. An interchangeable ultrasound transducer connector module (TCM) that can be pluggably coupled into an ultrasound control unit, comprising:

an ultrasound connector mounted on an external surface of an assembly, wherein the assembly has a predetermined configuration to mechanically mate with an opening in the ultrasound control unit; and a switching circuit mounted on an internal surface of the assembly, wherein the switching circuit electrically couples data lines in the ultrasound connector to a printed circuit board connector that can be plugged into a distribution bus within the ultrasound control unit, and wherein the switching circuit comprises a plurality of switches that can be activated and deactivated by the ultrasound control unit, wherein the plurality of switches are activated when the TCM is selected by the ultrasound control unit without receiving a user initiated TCM selection signal.

10. The interchangeable TCM of claim 9, wherein the predetermined configuration of the assembly mechanically mates to a standard personal computer 5¼ inch drive bay opening.

11. The interchangeable TCM of claim 9, wherein the assembly comprises:

a tray for mounting the switching circuit, and rails for slideably supporting the assembly in the ultrasound control unit.

12. The interchangeable TCM of claim 11, wherein the assembly further comprises a bezel for mounting the assembly to the opening in the ultrasound control unit.

13. The interchangeable TCM of claim 9, wherein each ultrasound connector utilizes a different number of data pins.

14. An ultrasound system, comprising:

a plurality of interchangeable transducer connector modules (TCMs), wherein each TCM includes an ultrasound connector, a switching circuit, and a pluggable interface; and an ultrasound control unit, wherein the ultrasound control unit includes:

a plurality of bays, each for receiving and pluggably coupling one of the TCMs into a distribution bus of the ultrasound control unit, and a system controller for selecting one of the plurality of TCMs and for activating the switching circuit of the system-selected TCM, wherein the system-selected TCM is selected by the system controller without the system receiving a user initiated TCM selection signal.

15. The ultrasound system of claim 14, wherein each TCM has a predetermined configuration to mechanically mate with each bay in the ultrasound control unit.

16. The ultrasound system of claim 15, wherein the predetermined configuration comprises a personal computer standard 5¼ inch drive bay opening.

17. The ultrasound system of claim 14, wherein the pluggable interface of each TCM comprises a first printed circuit board interface that can be pluggably coupled to a second printed circuit board interface in each bay.

18. The ultrasound system of claim 14, wherein the ultrasound control unit further comprising an enclosure to provide EMI shielding and mechanical support, and wherein the enclosure allows external access to the plurality of bays.

19. The ultrasound system of claim 14, wherein the system controller comprises a backplane having an interface for receiving a plurality of control boards.

20. The ultrasound system of claim 19, wherein the distribution bus is coupled to the backplane.

* * * * *